United States Patent [19]

Takamura

[11] Patent Number: 4,488,560
[45] Date of Patent: Dec. 18, 1984

[54] MENSTRUATION PERIODIC COUNTER

[75] Inventor: Takatsugu Takamura, Saitama, Japan

[73] Assignee: Colpo Company Limited, Tokyo, Japan

[21] Appl. No.: 416,709

[22] Filed: Sep. 10, 1982

[30] Foreign Application Priority Data

Sep. 19, 1981 [JP] Japan ................................ 56-148028

[51] Int. Cl.³ ............................................. A61B 5/00
[52] U.S. Cl. ..................................... 128/738; 128/736
[58] Field of Search ...................... 128/736, 738; 58/4; 364/417

[56] References Cited

U.S. PATENT DOCUMENTS

| 4,367,527 | 1/1983 | Desjacques | 128/738 |
| 4,396,020 | 8/1983 | Wolff et al. | 128/736 |

FOREIGN PATENT DOCUMENTS

| 2803152 | 7/1979 | Fed. Rep. of Germany | 128/738 |
| 2847397 | 5/1980 | Fed. Rep. of Germany | 128/738 |
| 2066528 | 7/1981 | United Kingdom | 128/736 |

OTHER PUBLICATIONS

Conference on Natural Family Planning, "Detection of Ovulation by the Basal Body Temperature Method" Chapter 13.
Parents July 1981, "Coitus Interruptus" pp. 68–74.

Primary Examiner—Kyle L. Howell
Assistant Examiner—Francis J. Jaworski
Attorney, Agent, or Firm—Browdy and Neimark

[57] ABSTRACT

A menstruation periodic counter is provided with an indicator of a calendar, an indicator of a bodily temperature chart and temperature measuring time, an input switch for receiving numeral values, and an alarm mechanism for sounding at a time set by the input switch, and wherein the calendar indicator indicates through a cursor information concerning the days obtained from the data for indicating the bodily temperature chart. Automatic adjustment of the range sensitivity of the temperature sensor and correction of out-of-range values, based on expected basal bodily temperature period as predicted by the Ogino method is effected by microprocessor.

5 Claims, 7 Drawing Figures

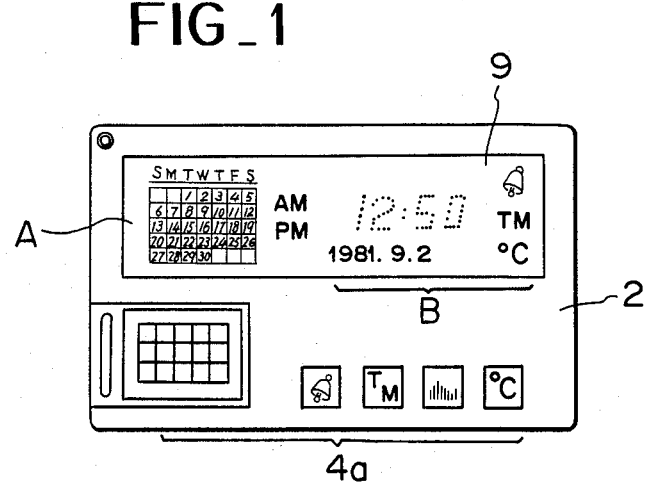
FIG_1
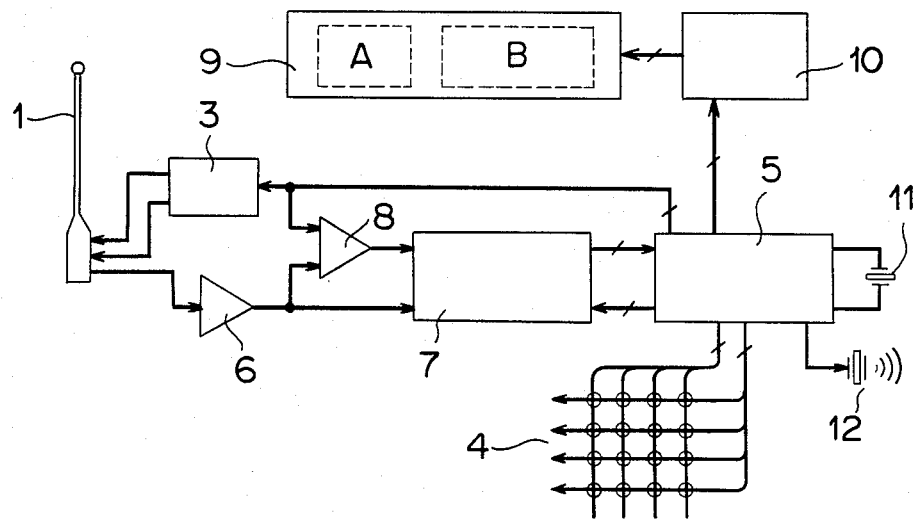
FIG_2
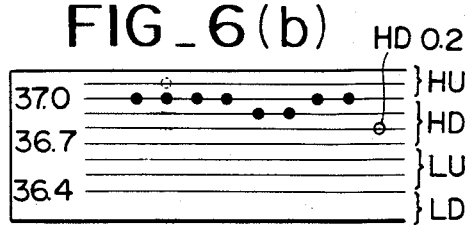
FIG_6(a)   FIG_6(b)

FIG_3

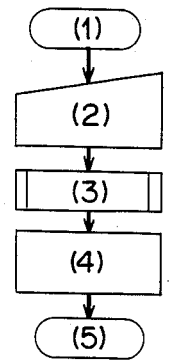

(1) Initial
(2) Inputting data of starting of previous menstruation
(3) Counting ovulation period
(4) Storing data of ovulation period in memory area
(5) Next

FIG_4

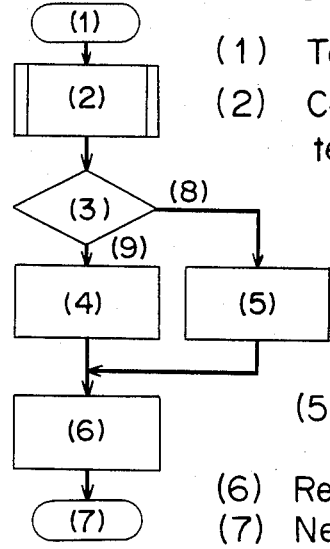

(1) Taking body temperature
(2) Counting routine of day-taking temperature
(3) Judging of range
(8) High temperature period
(9) Low temperature period
(4) Setting of ADC and probe at lower temperature range
(5) Setting of ADC and probe at high temperatature range
(6) Renealizing data and storing in memory area
(7) Next

FIG_5

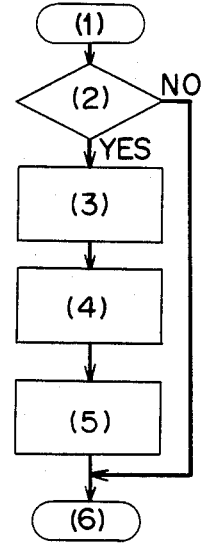

(1) In
(2) Is body temperatature than 30 samples?
(3) Referring to changing date from low temperatature period to high temperatature period
(4) Storing referred data (month, date) in ovulation period memory area
(5) Clearing integration counter of body temperatature data
(6) Next

MENSTRUATION PERIODIC COUNTER

FIELD OF INVENTION

The present invention relates to a menstruation periodic counter which is provided with an indicator of menstruation beginning day and an indicator of conceptive period and other functions.

BACKGROUND OF THE INVENTION

For methods of sensing the conceptive period, known are an Ogino's rhythm method of birth control and a basal bodily temperature method. However, it is troublesome in the former Ogino's method to count a certain period of days, and in the latter method to carefully take the bodily temperatures at determined time for long period of days and keep records of them. In addition, there has never been developed such a menstruation periodic counter of compact size which may indicate functionally values of data obtained from these methods.

SUMMARY OF THE INVENTION

In view of these circumstances, this invention is to provide a menstruation periodic counter which may functionally indicate the menstruation beginning date and the conceptive period.

The invention is concerned with the menstruation periodic counter which is characterized by providing an indicator of a calendar of each month, an indicator of a bodily temperature chart and temperature measuring time, an input switch for receiving numerical values, and an alarm mechanism for sounding at the time set by the input switch as demanded, the calendar indicator indicating, by a cursor, information concerning the days obtained from the data for indicating the bodily temperature chart.

Embodiment of the invention will be explained in reference to the attached drawings.

BRIEF DESCRIPTION OF THE DRAWINGS

FIG. 1 is a front view of one embodiment which embodies the invention into a device of a card shape, FIG. 2 is a block diagram of one embodiment of a counter by the invention, FIG. 3 is a flow chart showing an initial routine of the counter shown in FIG. 2, FIG. 4 is a flow chart showing a bodily temperature measuring routine, FIG. 5 is a flow chart showing an ovulation day routine, FIG. 6 (a) and (b) are explanatory views showing indications of the bodily temperatures.

In the drawings, the numeral 1 is a temperature measuring senser, 5 is a micro-processor, 7 is A-D converter, 8 is A-D converter control circuit, 9 is LCD indicator, 10 is LCD drive circuit, and 12 is a piezo-buzzer.

DESCRIPTION OF PREFERRED EMBODIMENTS

The attached drawings illustrate a preferable embodiment of the invention. FIG. 1 is a front view of one embodiment which embodies the invention into a device of a card shape. The numeral 9 is LCD indicator provided with liquid crystal indicating device, which comprises a calendar indicator A showing a calender of each month and an illustrator B showing the basal bodily temperature chart, time, day and the bodily temperature. FIG. 2 is a block diagram of one embodiment of a counter by the invention, and the numeral 1 is a temperature measuring sensor. The sensor may be such a kind which is directly bonded with sensor chip such as a silicon diode chip to a distributing wire board of flexible print of polyimide base, but for realizing a short time counting to be effected by the invention it is preferable to use thermistor in the sensor element. In the illustrated embodiment, three leads for bias electric current are included (for heating the temperature in the senser portion as mentioned later), a connector has three terminals for the three leads. The entire body is flexible to be pushed into a device 2, and on use it is taken out therefrom. The numeral 3 is a sensor heating circuit (sensor drive circuit) which in advance heats appropriately the temperature in the senser for enabling the short time counting. That is, a temperature measuring resistor has the characteristic that the resistance value of the element decreases as the temperature increases and it takes less time for measurement as the difference between ambient temperature of the sensor and the temperature to be measured decreases. Taking these points into consideration, if the element is in advance made electrically conductive up to, e.g., around 30° C. by self-heating, the measuring time is accelerated and it is possible to diminish the measuring time lag by means of the pro-heated ambient temperature. Actually, when a switch 4a disposed on a front face of the device of the card shape is pushed down, a circuit in a switch matrix 4 is formed, and when "thermometer" mode is designated, a microprocessor (MPU) 5 outputs the control signal of the temperature measuring range and moves to the bodily temperature measuring routine. The sensor drive circuit controls the bias electric current such that the sensor chip is rapidly heated up to, e.g., 30° C. The microprocessor 5 starts the temperature measuring monitor by means of the bodily temperature measuring routine program, calculates the temperature increasing rate of the senser, detects values treated stochastically (the bodily temperature of 63% in general), calculates real value (more than 98.5% in general) of the exact bodily temperature, and indicates them on LCD indicator 9. Through these relative treatments, time to be taken for measuring the bodily temperatures is largely decreased and the high precision measurement may be promised.

The numeral 6 is a pre-amplifier which appropriately effects DC amplification (current-voltage conversion amplification) on an analog signal sent from the temperature measuring sensor 1, and inputs it to A-D converter 7. For A-D converter, a double integral type of 8-bit binary output is used in general but others may be of course employed. The numeral 8 is A-D converter control circuit which controls standard voltage of A-D converter 7 and sets the temperature measuring range between 35° C. and 42° C. The output of A-D converter 7 is directly given to the micro-processor 5. The matrix in the switch matrix 4 is formed by the setting switch and the operation switch 4a, and the operation of the switch is read out in the micro-processor 5 by the switch monitor program. For the micro-processor 5, C-MOS -b 4-bit micro-computer may be used, and a drive circuit incorporating type may be also used. Other LCD may be of course used for the indicating element. Outputs from the micro-processor 5 are five systems of LCD indicating digit signal. LCD indicating segment signal, switching digit signal, piezo-buzzering drive signal, and bodily temperature measuring senser control signal. LCD indicator 9 is driven by the segment signal and the digit signal, and is lighted by, e.g., duty cycle of 1/32. LCD indicator 9 is arranged with the calender indicator A for indicating the calender of each month and the illustrator B for showing the basal bodily temperature chart. The illustrator B also may show the time, day, bodily temperature and others. If the digit signal is made 48 conditions and the duty cycle is made 1/50, the illustrator B can show days which change together with the temperature chart. 10 is LCD drive circuit, 11 is a liquid crystal vibrator, and 12 is a piezobuzzer. A-D converter control circuit 8 controls the standard voltage of A-D converter 7 to cause it to cover the temperature measuring range of 35° C. to 42° C. at the ordinary time of measuring temperature, and to cover any one of ranges of 35.5° C. to 37.5° C. (low temperature period) and 36.5° C. to 38.5° C. (high temperature period) at the time of the basal bodily temperature measurement. That is, if A-D converters of the same analyzing ability are used, the measuring precision is heightened by making narrow the range of measuring the temperatures and therefore the measurement of the basal bodily temperature in the low temperature period discriminated by the Ogino method is carried out in the range between 35.5° C. and 37.5° C., and the measurement of the basal bodily temperature is switched to the range between 36.5° C. and 38.5° C., and carried out there.

A next reference will be made to complementary compensation between an assumption method of ovulating period by the Ogino's counting method and a deciding method of ovulating days by the basal bodily temperature method. For example, assuming that it is January 1st today and the previous menstruation beginning day was December 20 last year, the last ovulating period of the women of the 28 day type-menstruation period is 5 days from December 4th to December 8th, and the ovulating period of this time is assumed as the 5 days from January 1st to 5th in dependence on the Ogino's method. These calculations are made by means of the micro-processor 5 by inputting the data of month and day from the key matrix 4a. The calculated results, i.e., the data of the ovulating period are stored in a memory which is provided with the micro-processor 5 (refer to FIG. 3). Since the ovulating period is assumed on January 1st, and when the basal bodily temperature is measured on that day, the measuring range is set in the range of the low temperature period (35.5° C. to 37.5° C.). If the measured temperature is outside of the determined scope due to the cold-fever or other reasons, linearization is made such that the measured temperature is automatically altered to near values to the assumed value, and stored in the memory. This flow chart is shown in FIG. 4. Similarly, the basal bodily temperature is measured, and when the data of more than 30 days are stored in the memory, the days of actually changing from the low temperature period to the high temperature period, i.e., the ovulating day or days are determined, and the data concerning this day are stored in the memory (refer to FIG. 5.). Subsequently, in dependence on this ovulating day the assumption days of the ovulating period by the Ogino's method are corrected as demanded. This correction is automatically made. When the switch 4a is operated, the basal bodily temperature chart and the menstruation periodic calender are illustrated on LCD indicator 9. On the calendar A maintaining the precision by the complementary compensation method, the conceptive period, the expecting days of a next menstruation beginning and others are illustrated by on-and-off of the cursor. Further, in respect to the basal bodily temperatures measured in the long period, the data of the last two months only are illustrated as the basal bodily temperature chart, and especially for effecting easy observation, an under mentioned treatment is prepared.

The average value of the high temperature period and the average value of the low temperature period are calculated, and the middle value therebetween is obtained and the temperature scale is illustrated (refer to FIG. 6). In FIG. 6(a), H is the average of the high temperature period, L is the average of the low temperature period, and Th is the middle value in order to provide "Th= $(H-L)/2+L$". On the other hand, with respect to the data of the basal bodily temperature, the difference from the average value is obtained and is indicated as an index. For example, assuming H: 37.0° C. and L: 36.4° C., Th (temperature threshold value)is 36.7° C. and when the data of the basal bodily temperatures in the memory range to be shown is 36.8° C., the indication index is obtained as follows:

$$36.7 - 36.8 = -0.1$$

Having a negative mark, it is the high temperature data (H)

$$37.0 - 36.8 = 0.2$$

Having no negative mark, it is below the average (D). That is, 36.8° C. of the basal bodily temperature data is an indicating index HD0.2, and this indication is as a white circle in FIG. 6(b). The data corresponding to the ranges of HU and LD are all H or L and the average value indication (for example, as the 2nd from the left in FIG. 6(b)). This is a rational and obvious indication method which pays attention to the fact that the most importance in the basal bodily temperature method is the repeating pattern of the low temperature period and the high temperature period, and the absolute value (actual temperature) is not so very important.

One of the embodiments according to the invention is incorporated with the piezo-buzzer 12 for the time signal, and when coming to the time of measuring the basal bodily temperature, the piezo-buzzer 12 is driven by tune for the measuring time and the micro-processor moves to the bodily temperature measuring routine. When the data obtained by the complementary compensation method are referred to, the temperature measuring range is devised for the correct measurement, and the measured data are preserved in the memory range of the basal bodily temperature data.

As was mentioned above, the present invention is arranged with the calender illustrator, the measuring time and the indicator of the basal bodily temperature chart on the same surface of the device. The calendar indicator shows through the cursor the next menstruation days obtained from the basal bodily temperature data and the conceptive period. The device of the invention is compact and convenient. If the alarm is furnished for the time of measuring the bodily temperature, the measurement may be speedy.

I claim:

1. A menstruation periodic counter, including a first indicator for indicating a calendar and a second indicator, and an operation switch comprising a switch for switching contents shown in the said second indicator and a switch for inputting numerical values, the counter comprising:

means for issuing an alarm at a time set by said numerical value inputting switch;

a temperature measuring sensor for measuring the basal bodily temperature of a subject when said alarm is issued;

an A-D converter for converting said basal bodily temperature measured by said temperature measuring sensor into a digital signal; and a microprocessor having a memory for storing digital signal outputs from said A-D converter;

said microprocessor calculating through application of Ogino's rhythm method, the conceptive period from a menstruation beginning data value input from said operation switch;

said microprocessor determining from the basal bodily temperature signals the conceptive period when the number of measurements made by said temperature measuring sensor exceeds a number representing the length in days of the menstruation period; and said microprocessor correcting the conceptive period calculated by said Ogino's method by the conceptive period determined from said basal bodily temperature outputs, and indicating the corrected conceptive period on the said first indicator, said microprocessor discriminating by using said Ogino's method and said menstruation beginning data value the condition of a high temperature or a low temperature period in the subject, and providing a signal indicative thereof, and means responsive to said signal for adjusting the output range of said A-D converter.

2. A menstruation periodic counter, including a first indicator for indicating a calendar and a second indicator, and an operation switch comprising a switch for swtiching contents shown in the said second indicator and a switch for inputting numerical values, the counter comprising:

means for issuing an alarm at a time set by said numerical value inputting switch;

a temperature measuring sensor for measuring the basal bodily temperature of a subject when said alarm is issued;

an A-D converter for converting said basal bodily temperature measured by said temperature measuring sensor into a digital signal; and a microprocessor having a memory for storing ditigal signal outputs from said A-D converter;

said microprocessor correcting the value of said digital signal if the basal bodily temperature exceeds a pre-determined range, and storing said corrected value in said memory as said basal bodily temperature signal, said mirroprocessor calculating through application of Ogino's rhythm method, the conceptive period from a menstruation beginning data value input from said operation switch;

said mirroprocessor determining from the basal bodily temperature signals the conceptive period when the number of measurements made by said temperature measuring sensor exceeds a number representing the length in days of the menstruation period; and said microprocessor correcting the conceptive period calculated by said Ogino's method by the conceptive period determined from said basal bodily temperature outputs and indicating the corrected conceptive period on the said first indicator.

3. A device as claimed in claim 2, further comprising a heating circuit for pre-heating the temperature measuring sensor prior to measuring of said basal bodily temperature.

4. A device as claimed in claim 1, wherein said microprocessor corrects the value of said digital signal if the basal bodily temperature exceeds a predetermined range, and stores said corrected value in said memory as said basal bodily temperature signal.

5. A device as claimed in claim 1, further comprising a heating circuit for pre-heating the temperature measuring sensor prior to measuring of said basal bodily temperature.

* * * * *